United States Patent [19]
Urbach et al.

[11] Patent Number: 5,282,475
[45] Date of Patent: Feb. 1, 1994

[54] APPARATUS AND METHOD FOR AUDIOMETRY

[76] Inventors: Doron Urbach, 51, Ein Ayalla 30825, Israel; Shlomo Gilat, 92 Emek Hefer Street, Netanya, Israel

[21] Appl. No.: 970,003

[22] Filed: Nov. 2, 1992

[30] Foreign Application Priority Data

Nov. 3, 1991 [IL] Israel .................................... 99946

[51] Int. Cl.⁵ ............................................ A61B 5/04
[52] U.S. Cl. ..................................... 128/731; 128/746
[58] Field of Search ................ 128/731, 746, 902, 732

[56] References Cited

U.S. PATENT DOCUMENTS

| | | | |
|---|---|---|---|
| 3,799,146 | 3/1974 | John et al. | 128/731 |
| 4,132,226 | 1/1979 | Seely et al. | |
| 4,201,224 | 5/1980 | John | 128/731 |
| 4,275,744 | 6/1981 | Thornton et al. | 128/746 |
| 4,462,411 | 7/1984 | Rickards | 128/746 |
| 4,488,610 | 12/1984 | Slavin | 128/746 |
| 4,550,736 | 11/1985 | Broughton et al. | 128/731 |
| 4,699,153 | 10/1987 | Shervin et al. | 128/731 |
| 4,736,751 | 4/1988 | Gevins et al. | 128/732 |
| 4,847,763 | 7/1989 | Moser et al. | 128/746 |
| 4,913,160 | 4/1990 | John | 128/746 |
| 4,932,416 | 6/1990 | Rosenfeld | 128/731 |
| 5,137,027 | 8/1992 | Rosenfeld | 128/746 |

OTHER PUBLICATIONS

Kutas, M. & Hillyard, S. A. (1988) "Contextual effects in language ...". Plum, F. ed., Language, Communication and Brain. Raven Press, New York. pp. 87-100.

McCallum et al. (1984) "The effect of physical and semant incongruities on auditory event related potentials". Elec encephalogr. Clin. Neurophysiol., 59, 477-488.

Primary Examiner—Max Hindenburg
Attorney, Agent, or Firm—Ladas & Parry

[57] ABSTRACT

Apparatus for objective determination of auditory thresholds for intelligible speech in a human subject including apparatus for presenting a sequence of at least one intelligible speech stimuli to a human subject at a respective sequence of stimulus intensities, and apparatus for monitoring at least one physiological response of the human subject that varies with the human subject's reception of each stimulus.

24 Claims, 7 Drawing Sheets

$F_Z$ = FRONTAL ZONE
$C_Z$ = CENTRAL ZONE
$P_Z$ = PARIETAL ZONE

FIG. 7

$F_Z$ = FRONTAL ZONE
$C_Z$ = CENTRAL ZONE
$P_Z$ = PARIETAL ZONE

FIG.8

Fz = FRONTAL ZONE
Cz = CENTRAL ZONE
Pz = PARIETAL ZONE

FIG.9

Fz = FRONTAL ZONE
Cz = CENTRAL ZONE
Pz = PARIETAL ZONE

APPARATUS AND METHOD FOR AUDIOMETRY

FIELD OF THE INVENTION

The present invention relates generally to methods and apparatus for audiometry and more particularly to methods and apparatus for determination of an auditory threshold for intelligible speech.

BACKGROUND OF THE INVENTION

Tests determining auditory thresholds in human subjects are well known in the art. Typically these tests include the presentation to a subject of a signal, typically a pure tone, over a range of signal intensities and recording the lowest intensity at which the subject reports that he hears the signal. This report typically includes a voluntary response such as pressing a button or raising a hand.

Also known in the art are tests determining auditory thresholds for intelligible speech. These tests determine the minimum intensity at which an auditory stimulus, consisting of spoken meaningful words, must be presented for the words to be heard and understood. Typically, tests determining the auditory threshold of intelligible speech include presenting a stimulus including spoken words to a subject over a range of intensities, having the subject repeat the words he hears, and recording the lowest intensity at which the words are correctly repeated.

It is well established that electrical patterns of the human brain, as recorded in an electroencephalogram (EEG), can reflect cognitive processes. For example, Kutas, M. and Hillyard, S. A. (1988, Contextual effects in language comprehension Studies using event-related brain potentials. In Plum, F. ed., Language, communication and the brain. Raven Press, New York) have studied event related potentials (ERP's) in the EEG pattern in relation to contextual effects in language comprehension. These authors have reported that when human subjects are presented with a sentence on a CRT display and the last word of the sentence is incongruent (i.e. does not make sense in the context of the sentence) the subjects show a specific ERP. This ERP, which is called N400, is a slow negative potential peaking at about 400 msec from the presentation of the last word. This N400 response is not present in subjects presented with a sentence that ends in a congruent word (i.e. a word that makes sense in the context of the sentence).

Similar results have been reported by McCallum et al. (1984, The effect of physical and semantic incongruities on auditory event related potentials. Electroencephalogr. Clin. Neurophysiol., 59, 477–488) with respect to auditory stimuli. These results suggest that N400 ERP's are the subjects' response to incongruity in language, regardless of whether the language is written or spoken.

SUMMARY OF THE INVENTION

An object of the present invention is to provide an improved method and apparatus for objective measurement of an auditory threshold to intelligible speech in human subjects.

There is thus provided, in accordance with a preferred embodiment of the present invention, apparatus for objective determination of auditory thresholds for intelligible speech in a human subject including apparatus for presenting a sequence of at least one intelligible speech stimuli to a human subject at a respective sequence of stimulus intensities, and apparatus for monitoring at least one physiological response of the human subject that varies with the human subject's perception of each stimulus.

Further in accordance with a preferred embodiment of the present invention, the apparatus for presenting includes a microprocessor for storage and recall of at least one digital stimulus signal, and a digital to analog converter to convert the at least one digital stimulus signal to at least one analog stimulus signal.

Still further in accordance with a preferred embodiment of the present invention, the apparatus for presenting additionally includes apparatus for random selection of one of a plurality of digital stimuli.

Additionally in accordance with a preferred embodiment of the present invention, the apparatus for presenting includes a stimulus signal amplifier for selectively amplifying the at least one analog stimulus signal to a predetermined stimulus signal intensity.

Further in accordance with a preferred embodiment of the present invention, the apparatus for monitoring includes a plurality of scalp electrodes operative to monitor electrical brain activity.

Still further in accordance with a preferred embodiment of the present invention, apparatus for display of the monitored physiological response to a human operator is also provided, so as to enable the human operator to detect known physiological response profiles.

Additionally in accordance with a preferred embodiment of the present invention, the apparatus for display includes a CRT display.

Further in accordance with a preferred embodiment of the present invention, the apparatus for monitoring additionally includes apparatus for correcting the monitored physiological response by substantially removing measurement artifacts.

Still further in accordance with a preferred embodiment of the present invention, the apparatus for correcting includes a suborbital electrode operative to detect electrical activity correlated with eye movements and eye blinks.

Additionally in accordance with a preferred embodiment of the present invention, the at least one physiological response to a presented stimulus takes a known EEG waveform when the subject understands the stimulus.

Still further in accordance with a preferred embodiment of the present invention, the known EEG waveform includes the N400 wave form.

There is also provided, in accordance with another preferred embodiment of the present invention, a method for objective determination of auditory thresholds for intelligible speech in a human subject including the steps of presenting a sequence of at least one intelligible speech stimuli to a human subject at a respective sequence of stimulus intensities, and monitoring at least one physiological response of the human subject that varies with the human subject's perception of each stimulus.

Further in accordance with a preferred embodiment of the present invention, the step of presenting includes the steps of storing and recalling at least one digital stimulus signal, and converting the at least one digital stimulus signal to at least one analog stimulus signal.

Still further in accordance with a preferred embodiment of the present invention, the step of presenting additionally includes the step of random selection of one of a plurality of digital stimuli.

Additionally in accordance with a preferred embodiment of the present invention, the step of presenting includes the step of selectively amplifying the at least one analog stimulus signal to a predetermined stimulus signal intensity.

Further in accordance with a preferred embodiment of the present invention, the step of monitoring includes the step of providing a plurality of scalp electrodes operative to monitor electrical brain activity.

Still further in accordance with a preferred embodiment of the present invention, the method also includes the step of displaying the monitored physiological response to a human operator, so as to enable the human operator to detect known physiological response profiles.

Additionally in accordance with a preferred embodiment of the present invention, the step of displaying includes providing a CRT display.

Still further in accordance with a preferred embodiment of the present invention, the step of monitoring additionally includes the step of correcting the monitored physiological response by substantially removing measurement artifacts.

Further in accordance with a preferred embodiment of the present invention, the step of correcting includes the step of providing a suborbital electrode operative to detect electrical activity correlated with eye movements and eye blinks.

Further in accordance with a preferred embodiment of the present invention, at least one physiological response to a presented stimulus takes a known EEG waveform, such as the N400 waveform, when the subject understands the stimulus.

BRIEF DESCRIPTION OF THE DRAWINGS

The present invention will be understood and appreciated more fully from the following detailed description taken in conjunction with the drawings in which.

DETAILED DESCRIPTION OF PREFERRED EMBODIMENT

Figure 1:
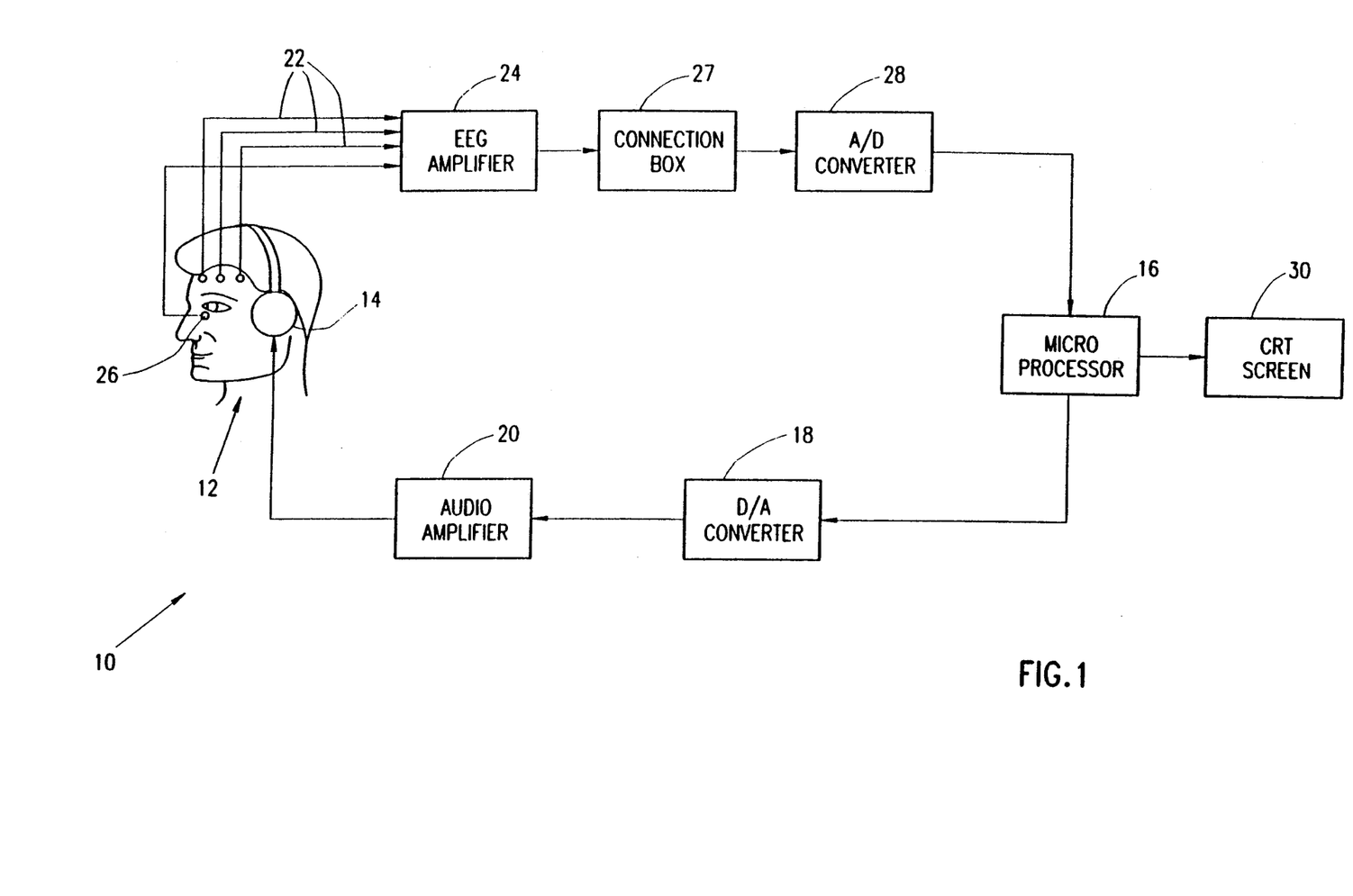
FIG. 1 is a block diagram illustration of apparatus for determination of auditory thresholds for intelligible speech in human subjects which is constructed and operative in accordance with a preferred embodiment of the present invention.

Reference is now made to FIG. 1 which illustrates apparatus 10 for objective determination of auditory thresholds for intelligible speech in human subjects. In apparatus 10, intelligible speech auditory stimuli which vary in intensity are sequentially presented to either or both ears of a human subject 12, through earphones 14. The intelligible speech auditory stimulus may be produced by any suitable conventional apparatus such as the following apparatus:

A microprocessor 16 outputs an intelligible speech digital signal that is converted to an analog signal by digital to analog converter 18. The analog signal is in turn amplified by an audio amplifier 20 which provides an analog stimulus signal of selectable intensity to the earphones 14.

The subject's EEG response to the stimuli is typically sensed by scalp electrodes 22 each of which is connected to one channel of a multichannel EEG amplifier 24 which produces an amplified electrical response signal for each channel. Preferably, a suborbital electrode 26 senses the electrical potential associated with eye movement and eye blink artifacts. One channel of the multichannel EEG amplifier also receives input from the suborbital electrode and outputs an amplified correction signal.

The amplified electrical response signals and the amplified correction signal are imputed to a connection box 27 which provides a connection between each channel of the multichannel EEG amplifier 24 and an analog to digital converter 28. The analog to digital converter 28 produces a digital response signal for each of the amplified response signals and a digital correction signal for the amplified correction signal and inputs the digital signals to the microprocessor 16 for storage.

The microprocessor 16 recalls the digital signals, corrects the digital response signal using the digital correction signal and provides a digital response signal or signals or a corrected digital response signal or signals to a CRT screen 30 which displays the digital response signal as a visual image or trace of the sensed EEG. Visual observation of an EEG trace on the CRT screen 30 is then used to determine whether the trace has a particular form such as an N400 ERP. The presence of the N400 ERP response indicates that the subject has heard and perceived the intelligible speech stimulus.

A preferred implementation, based on commercially available elements, of the apparatus of FIG. 1 is now described.

The microprocessor 16 typically comprises an IBM-/AT with a Deico PC-286i Motherboard (commercially available from Deico Electronics Inc, Fremont, Calif., U.S.A.) running at 20 MHz. Microprocessor 16 may be associated with an 8 Mbyte RAM disk used as an expanded memory, a 40 Mbyte hard disk (Western Digital WD93094A), a 1.2 Mbyte floppy disk commercially available from Teak Corp, 3-7-3 Naka-Cho Musashino, Tokyo, Japan, and a mathematical chip 80287 (commercially available from Integrated Information Technology Inc., Mission College Blvd., Santa Clara, U.S.A.).

The intelligible speech stimuli, which are typically spoken words, groups of words or sentences, are typically imputed to the microprocessor 16 from an audiotape recording. The audiotape is typically prepared by having a female speaker read the stimuli loudly and then recording the spoken stimuli on audiotape using a recorder such as a DE-10 commercially available from Hitachi, Minato Ku Tokyo 105 Japan. The stimuli are then sampled by the microprocessor 16, typically one word at a time, at a suitable rate such as 25 KHz, through an analog to digital converter (such as an RTI 815A, commercially available from Analog Devices Inc., Technology Way Nord Mass. U.S.A.), and are typically stored on the hard disk.

The stimuli are typically played back by accessing the stimuli stored in the microprocessor 16 to provide a digital signal to digital to analog converter 18 which may be a PCI-20006M 16 bit 2-channel Burr-Brown 1141 card, commercially available from Burr-Brown, Tucson, Ariz., U.S.A. The stimuli may be accessed as individual words, as individual words in a specific order, as groups of words in a sentence or set of words, or as sentences or sets of words in a specific order.

The analog output of digital to analog converter 18 is typically provided via a carrier and module in socket 3 to audio amplifier 20. For example, a PCI-20041C-A carrier and a PCI-20341M module, both commercially available from Analog Devices Inc, Technology Way Nord, Mass., U.S.A. may be employed and audio amplifier 20 may be a Kenwood stereo integrated amplifier model KA-3300 (commercially available from Kenwood, New Lane Havart Hampshire PO92NH England). The audio amplifier 20 produces an analog stimulus signal which is provided to earphones 12, such as TDH50P earphones (commercially available from Grason Stadler, 537 Great Road Littleton Mass. 01460 U.S.A.).

The amplitude of the analog stimulus signal is determined either manually, by manually adjusting the amplifier 20, or automatically, by the microprocessor 16, which determines the intensity of the auditory stimulus presented to the subject. The auditory stimulus may be presented at any suitable range of intensities, such as intensities between 25 and 100 db.

The monitoring of the subject's EEG pattern is typically initiated when the stimulus is presented and continues for a suitable period of time such as 1500 millisec. The subject's EEG response to the stimuli is typically sensed by the three scalp electrodes 22, one of which is in the frontal region (fz), one in the central region (cz) and one in the parietal region (pz). The electrodes are typically held in place with an elastic cap (commercially available from Electro-Cap International, Eaton, Ohio, U.S.A.).

The electrical potential associated with eyeblink and eye movement is often a component of the EEG response which masks the presence of an ERP. Eye blink-/movement potential may be sensed by suborbitally placed standard electrode 26.

All electrodes 22 and 26 are referred to a standard electrode attached to the left ear lobe to provide a reference for bipolar deviations. Also, a standard ground electrode may be connected to the left hand. Standard electrodes are commercially available from Electro Cap International, Eaton, Ohio, U.S.A.

All of electrodes 22 and 26 are typically connected to the multichannel EEG amplifier 24. Amplifier 24 may, for example, comprise a Grass Model P-511 and may be associated with a power supply (Grass Instruments Company, Quincy, Mass., U.S.A.). The scalp electrodes 22 and the suborbital electrode 26 are typically each connected to a separate channel of multichannel EEG amplifier 24, while the reference and ground electrodes are typically connected to each channel of multichannel EEG amplifier 24.

The input from each electrode is typically passed through a low cut off (0.03 Hz) and a high cut off (100 Hz) filter of the multichannel EEG amplifier 24. Each channel of the multichannel EEG amplifier 24 is typically connected to connection box 27. Connection box 27 acts as an interface between the EEG amplifier 24 and the audio to digital converter 28. Converter 28 is typically an RTI 815 12 bit 16 channel card (commercially available from Analog Devices Inc, Technology Way Nord, Mass. U.S.A.), for the IBM A/T. The following configuration may be employed: J1 pin 25 connected to W16 Pin A, and address 390H, single ended, two's complement and bipolar ±10 V selected. The digital response signal produced by audio to digital converter 28 is typically sampled by microprocessor 16 at the rate of 250 Hz.

The monitored EEG responses are typically stored on the hard disk of the microprocessor 16 as single records. Each signal is typically labeled so as to identify the stimulus to which it is the response and the intensity of the stimulus or stimulus portion is also stored. All monitored EEG responses are typically visually scanned by a human observer to determine if an ERP is present in the EEG record. Alternatively, the presence of an ERP can be determined by a microprocessor using conventional signal analysis methods.

Two types of stimuli are typically employed: calibration stimuli and test stimuli. Calibration stimuli are employed to determine that the apparatus is functioning correctly, that the subject can clearly hear suprathreshold stimuli, that ERP's can be detected, and that the subject can produce an indicative ERP such as N400 to specific incongruent suprathreshold auditory stimuli. Calibration methods and stimuli are described in detail below.

Test stimuli are employed to determine the auditory threshold for intelligible speech and are typically those stimuli for which it has been determined that the subject can produce an indicative ERP such as N400, if the stimulus is heard and understood.

Figure 2A:
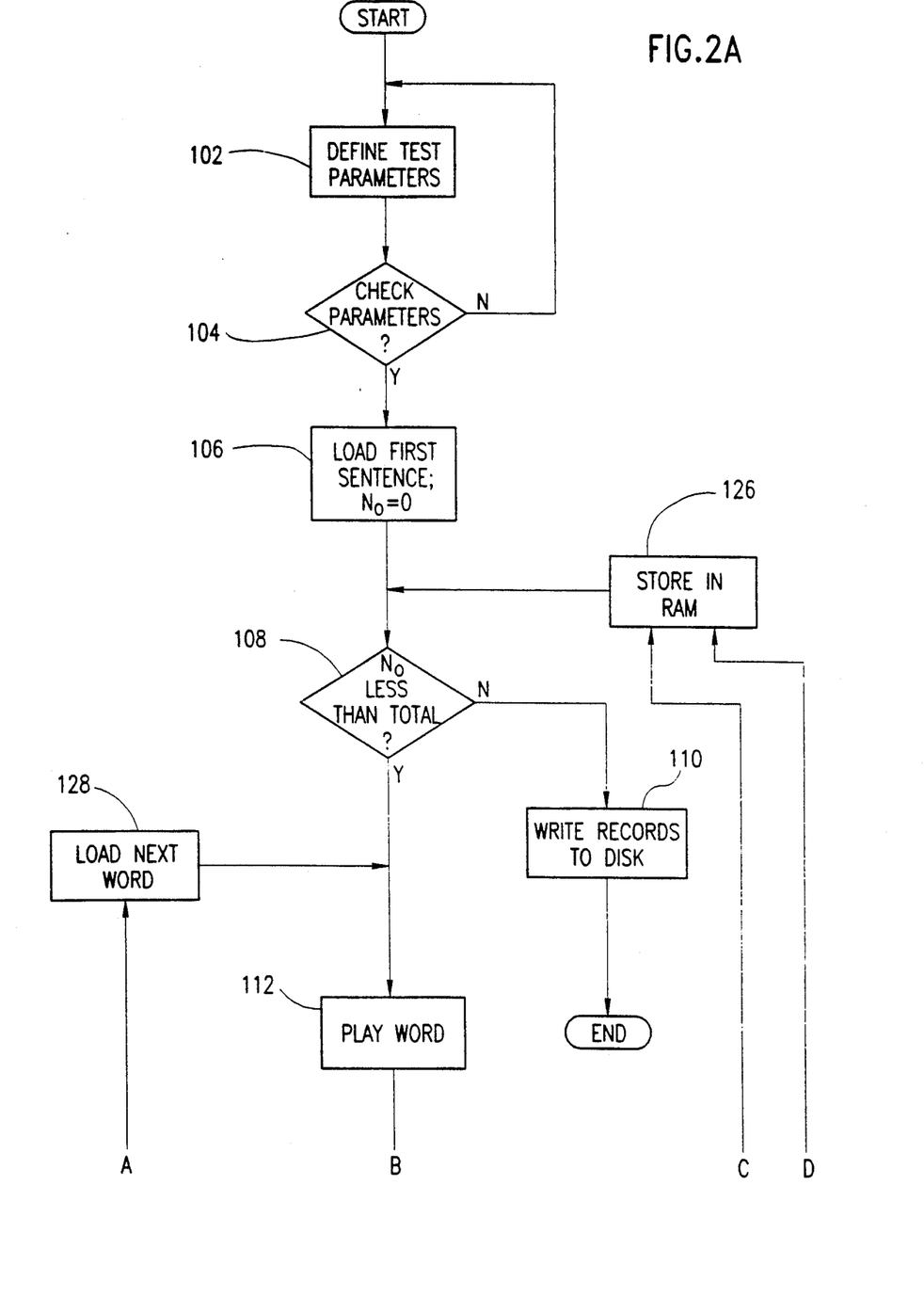
FIGS. 2A and 2B constitute a flow chart illustration of a method for determination of auditory thresholds for intelligible speech in human subjects which is operative in accordance with a preferred embodiment of the present invention.
Figure 2B:
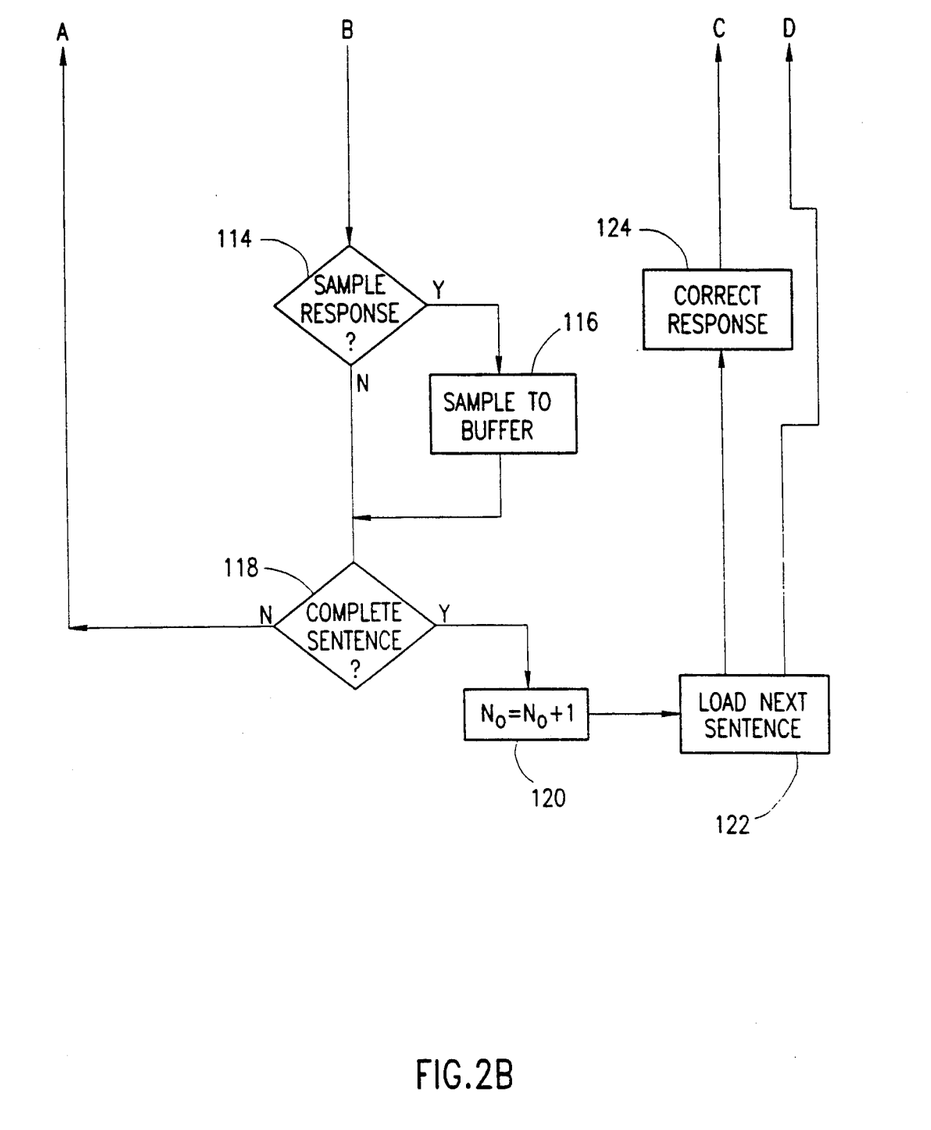

Reference is now made to FIGS. 2A and 2B which constitute a flow chart that illustrates a preferred method for determination of an auditory threshold for intelligible speech in human subjects.

The procedure is initiated in step 102 with the user inputting test parameters into microprocessor 16 of FIG. 1. Test parameters may include: the number of trials (i.e. stimulus presentations) in a test sequence, the stimuli to be used in the test sequence, the order in which the stimuli are to be presented, the speed of presentation, the interstimulus interval, the length of time over which the EEG is sampled, the rate of sampling of the EEG, the number of EEG channels to be recorded, the response record file name, the number of responses to be recorded, the intensity of the stimulus or stimulus portion and, if a stimulus is to be presented at more than one intensity level, the stimulus intensity of each presentation.

The parameters are then reviewed by the user in step 104 and if they are correct the test sequence is initiated. If they are not correct the user returns to step 102.

Once the test sequence is initiated (step 106) the first stimulus or stimulus portion is loaded from the RAM disk microprocessor 16 to memory and a stimulus counter, $N_0$, is set to zero. Each stimulus is typically a word or a sentence or set of words. For sentence stimuli, each word of the sentence is termed herein a "stimulus portion". Words are loaded one by one from the RAM disk.

After the first word is loaded in step 106, step 108 checks whether the number of trials already presented in the test sequence, $N_0$, is still less than the total number of trials in the test sequence as defined in step 102.

If $N_0$ has reached the total number of trials, i.e. the last stimulus of the test has just been played, the test sequence is ended. In step 110, the recorded EEG response, preferably both uncorrected for eye movement/blink and corrected, as explained below, is copied from the RAM disk to a hard-disk and is saved for subsequent analysis and display on CRT 30 of FIG. 1.

If the test sequence continues, because $N_0$ is still less than the predetermined total number of trials, step 112 is initiated in which the next stimulus or stimulus portion is recalled and presented.

Step 114 checks if the EEG response should be recorded. Typically, recording only takes place when the incongruent word in an incongruent stimulus is presented or when a corresponding congruent word in a corresponding congruent stimulus is presented, as explained in more detail below.

If recording is to take place, i.e. if the current word is incongruent or corresponds to an incongruent word in a corresponding incongruent stimulus, the procedure continues with step 116 which initiates recording upon presentation of the stimulus or stimulus portion and continues recording for a predetermined period of time.

If recording is not begun or when recording has ended, step 118 determines if the complete stimulus has been presented. If so, the stimulus counter $N_0$ is incremented by 1 (step 120), the next stimulus or the first portion of the next stimulus is loaded to memory from the RAM disk (step 122), the response recorded in step 116 is corrected for eye movement and eye blink artifacts (step 124) and the corrected and non-corrected responses are stored on the RAM disk (step 126). The procedure then returns to step 108.

If the complete stimulus has not been presented, typically when the stimulus is a sentence or word set, only some of whose words have been presented, the next word is loaded from the RAM disk (step 128) and the procedure returns to step 112.

A listing of object code generated on an IBM AT running the disk operating system (DOS) and implementing the procedures described herein above is appended hereto and is referenced Annex A.

Figure 3:
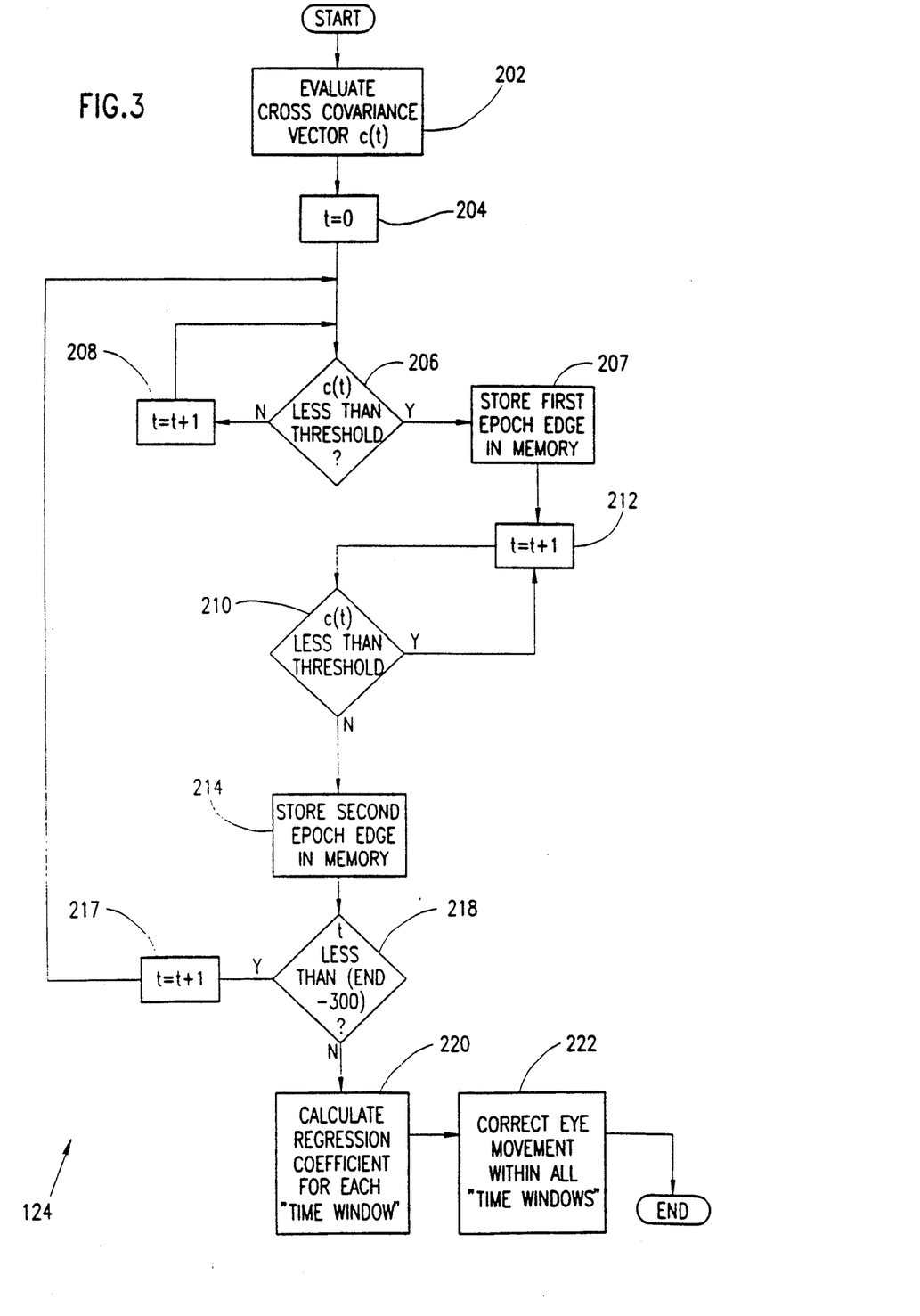
FIG. 3 is a flow chart illustration of a method suitable for implementing one of the steps of the method of FIGS. 2A and 2B.

Reference is now made to FIG. 3 which illustrates a method for correction for eye movement artifacts which is suitable for implementing step 124 in FIG. 2. The correction of individual ERP's carried out by the method of FIG. 3 is limited to epochs in which vertical eye movement, also termed herein "eye movement", and eye blink are found to be high enough to contaminate the ERP. The method detects presence of eye blink and vertical eye movements by taking advantage of the fact that eye blink and eye movements generate opposite potential deflections in ET (eye top) relative to EB (eye bottom) electrodes when the recordings from the ET and EB electrodes are referenced to the mastoid bone. An EB electrode is not affected by frontal brain activity because of its distance from the frontal lobe.

In the method of FIG. 3, readings are obtained from ET and EB electrodes. A cross covariance vector is computed within a moving window of 300 msec, reflecting the relationships between activity recorded in electrodes EB and ET. The cross covariance information is employed to identify eye movement/blink epochs defined as time segments in which the EB to ET cross covariance exceeds a predetermined negative threshold such as $-0.3$. The threshold is preferably selected to correspond in magnitude to the amount of noise in the system.

Corrected ERP signals (ERPc) for each lead within each eye movement/eye blink epoch is performed by subtracting the EB electrode recordings (EB), multiplied by linear regression coefficients K, from the raw or uncorrected ERP signals (ERPr), for each electrode site:

$$ERPc = ERPr - K * EB,$$

where the linear regression coefficients K are computed for each electrode site as follows:

$$K = \frac{P * \mathrm{sum}(ERPr * EB) - \mathrm{sum}(ERPr) * \mathrm{sum}(EB)}{P * \mathrm{sum}(ERPr * ERPr) - \mathrm{sum}(ERPr) * \mathrm{sum}(ERPr)}$$

where:
P = number of points in each window. For example there are 75 points if 300 msec windows are employed and the dwell time is 4 msec.

Response correction is performed separately for each of the scalp electrode recordings.

The method of FIG. 3 includes the following steps:

Step 202—compute a cross covariance vector c(t) reflecting the relationship between eye top activity to eye bottom activity.

Step 204—Initially, t=0.

Step 206—Until c(t) is found to be less than the predetermined threshold, such as $-0.3$, keep incrementing (step 208). When c(t) is found to be less than $-0.3$, an eye movement/blink has been found, so the beginning or first edge of an epoch is stored in memory (step 207). While c(t) remains less than $-0.3$ (step 210), keep incrementing (step 212). When c(t) is no longer less than $-0.3$, the eye movement/blink has terminated, so the end or second edge of the epoch is stored in memory (step 214).

More epochs are searched for by incrementing t (step 217) and then repeating from step 206 on, until (step 218) t is so large that no complete 300 msec windows remain. At this point, the regression coefficient K is computed, as explained above, and the EEG response is corrected for any eye movements encountered, also as explained above.

A listing of object code generated on an IBM AT running the disk operating system (DOS) and implementing the method of FIG. 3 as described herein is appended herein and is referenced Annex B.

Figure 4:
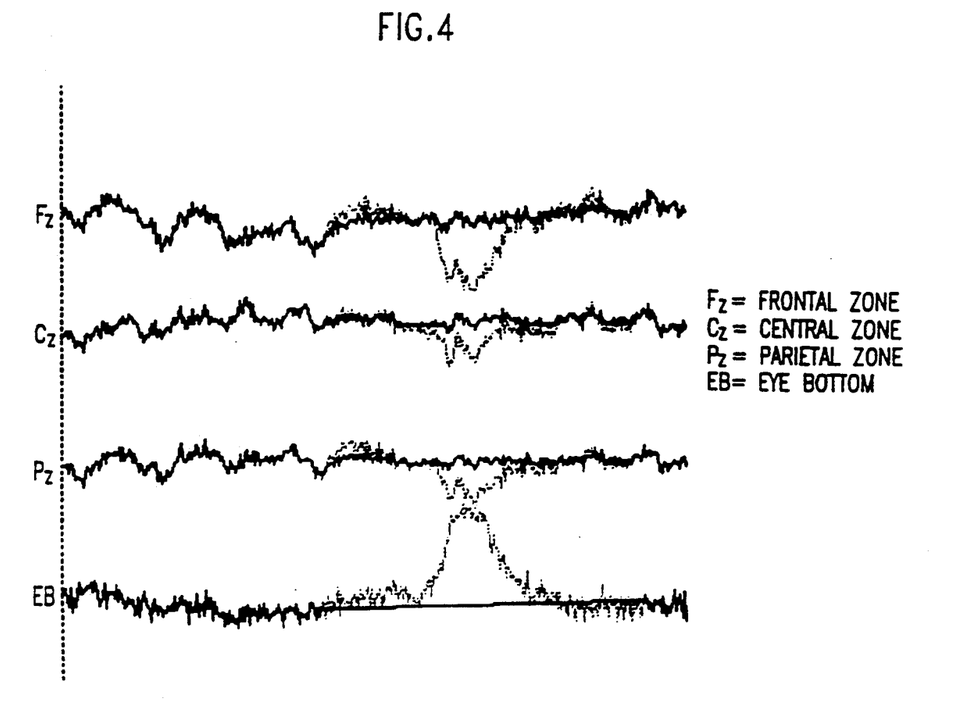
FIG. 4 shows an EEG recording of a subject's EEG response when corrected for eye movement (dark trace) and when uncorrected for eye movement (light trace), the direction of negativity being upward from the base line.

The results of the above correction procedure can be seen in FIG. 4 which shows both the corrected (dark trace) and uncorrected (light trace) EEG response for three scalp electrodes $F_z$, $C_z$ and $P_z$.

Three examples of calibration stimuli and procedures are now described.

a) The "Odd Ball" procedure, described in the following publication, the disclosure of which is incorporated herein by reference:

Barry, S. and Oken, M. D., "Endogenous event related potentials", in Chiappa, K. H. (Ed.): Evoked potentials in clinical medicine. Raven Press 1990.

The Odd Ball procedure is used to detect problems associated with the system or the recordings such as noise interference, poor electrode mounting, and incorrect system configuration. The procedure also confirms that ERP's can be detected.

In the Odd Ball procedure the subject is presented with suprathreshold auditory stimuli words. In the first part of the test one word, such as Red, is repeatedly presented to the subject and another word, such as Green, is occasionally presented, interspersed at random points during the repeated presentation of the word Red. The subject is instructed to count the occurrences of the word Green. In the second part of the test, the roles of Red and Green are reversed.

An average, over both parts, of the subject's EEG responses to the occasionally presented word is compared to the average, over both parts, of his responses to the repeatedly presented word, to determine whether the P300 wave form is present in response to the occasionally presented word. The P300 wave form is a positive EEG deflection which occurs about 300 msec after stimulus onset and is indicative of a subject's attention to the stimulus.

b) The "Last word in list" procedure: Determines whether a subject can produce an N400 response to an incongruent auditory stimulus.

Sets of three semantically related words are formed, and a last word is added to each set to form either a congruent set, in which the fourth word is semantically related to the first three, or an incongruent set, where the fourth word is not semantically related to the first three. The congruent and incongruent sets are presented to the subject as auditory stimuli at suprathreshold intensities. The EEG responses of the subject are examined to determine if the N400 wave form is present when the incongruent sets are presented.

A sample list of congruent and incongruent sets is the following:

Congruent

1. Car, Plane, Ship, Motorcycle.
2. Knife, Fork, Spoon, Plate.
3. Horse, Cat, Dog, Donkey.
4. A, B, C, D.
5. Orange, Apple, Banana, Lemon.
6. Seven, Ten, Five, Three.
7. Red, Blue, Yellow, Green.

Incongruent

1. Car, Plane, Ship, Red.
2. Horse, Cat, Dog, D.
3. Knife, Fork, Spoon, Donkey.
4. Red, Blue, Yellow, Plate.
5. Orange, Apple, Banana, Three.
6. Seven, Ten, Five, Lemon.
7. Red, Blue, Yellow, Motorcycle.

c. "Last word in sentence" procedure:

Confirms that a subject can produce an N400 response to an incongruent auditory stimulus.

Sentences are prepared in which the last word makes sense in the context of the sentence (congruent sentences) or does not make sense in the context of the sentence (incongruent). Typically there are several sentences for each final word, some congruent and others incongruent.

A sequence of interspersed congruent and incongruent sentences are presented to the subject as auditory stimuli at suprathreshold intensities. The EEG responses of the subject are examined to determine if the N400 wave form is present when incongruent stimuli are presented.

Sample sentences are as follows:

Congruent

1. I drink coffee with milk.
2. Her dress is made of silk.
3. I like chocolate milk.
4. I bought a liter of milk.
5. Her hair is as soft as silk.
6. Parachutes were once made of silk.
7. My dog has a tail.
8. The red kite has a white tail.
9. I am waiting for a letter in the mail.
10. The boat has a white sail.

Incongruent

1. I drink coffee with silk.
2. Her dress is made of milk.
3. I like chocolate silk.
4. I bought a liter of bilk.
5. Her hair is as soft as bilk.
6. Parachutes were once made of bilk.
7. My dog has a sail.
8. The red kite has a white mail.
9. I am waiting for a letter in the tail.
10. The boat has a white tail.

Sentences like the above may be used as test stimuli in the method of FIGS. 2A and 2B. The sentences are presented as auditory stimuli with the last word in the sentence at subthreshold intensities. The intensity of the last word is gradually increased over stimuli until the last word is suprathreshold. The EEG records are examined for the lowest intensity at which the N400 waveform appears. The N400 response is expected to appear only after presentation of an incongruent word. Therefore, any appearance of N400 to a congruent word is assumed to be an artifact and the test series is repeated.

The stimulus intensity at which the incongruent word is first heard and perceived is the auditory threshold for that word. The auditory threshold for intelligible speech is computed by averaging, over the various stimuli, the minimum intensity which produces an N400 response to an incongruent stimulus.

FIGS. 5-9 illustrate sample results obtained in the course of determining the auditory threshold for intelligible speech in an individual subject. To obtain the results of FIGS. 5-9, the apparatus and procedures described above were employed for a male subject 25 years of age with no known hearing problem.

Specifically, the subject was seated and the electrodes connected to his scalp. Resistance between any two electrodes was kept below 5 Kilo-Ohms by using ECI Electro-Gel TM commercially available from Electro Cap International Inc., Eaton, Ohio, U.S.A. The EEG response was monitored at the following sites: Fz, Cz, and Pz, as defined by the International 10/20 Electrodes Placement System (Jasper, H. H., 1958, 110/10 Electrode System of the International Federation, Electroencephalogr. Clin. Neurophysiol., 10, 371-375)). These electrodes used the left ear lobe as a reference for bipolar derivations. A ground electrode was connected to the left hand. Earphones were placed on the subject's ears, but only one ear was tested.

Prior to testing, all words were loaded to a RAM disk. Sentences were then presented to the subject through earphones in a clear and comprehensible manner. Sampling the EEG and transmission of the incongruent or congruent word began simultaneously. The EEG's were recorded over 1500 milliseconds and filtered to 0.03-100 Hz by an analog filter. The signal was then sampled at a rate of 250 Hz. Only EEG's which corresponded to the presentation of a congruent or incongruent word were recorded. During the presentation of the test stimuli, intensity variations of the stimulus was performed by software.

The test procedure included two stages, calibration and detection of auditory threshold to intelligible speech. The calibration stage itself included three stages, which followed the "Odd Ball", "Last Word in List" and "Last Word in Sentence" procedures, all described above, respectively.

Figure 5:
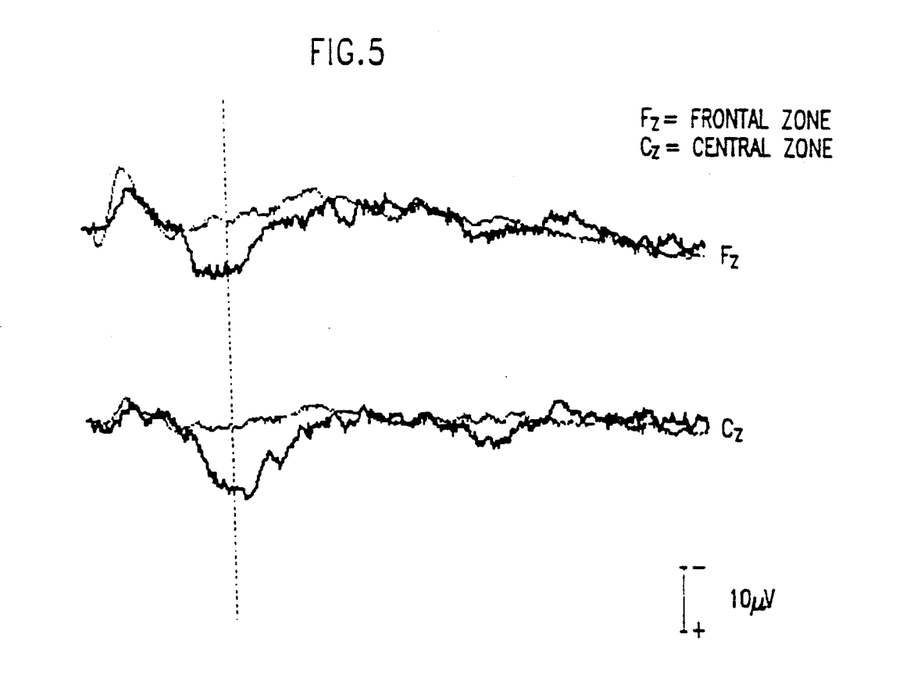
FIG. 5 shows a corrected EEG recording of a subject's response for the first 1500 msec following presentation of the beginning of a "rare" word in an "odd ball" calibration procedure with the dark trace being a typical response to a rare word, the light trace being a response to a "common" word and the direction of negativity being upward from the base line.
Figure 6:
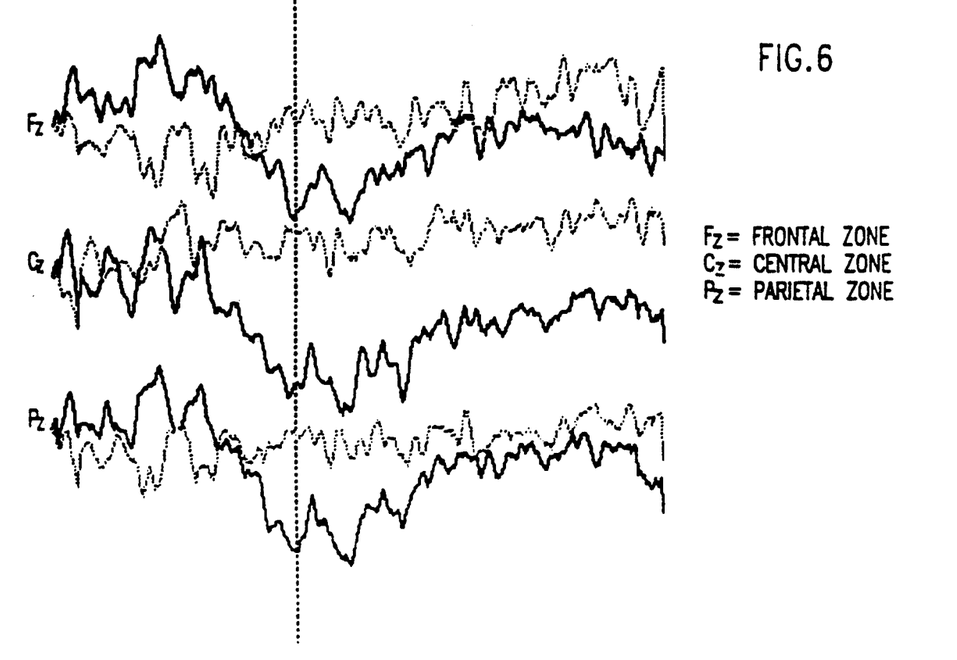
FIG. 6 shows a subject's typical EEG response, corrected for eye movement, in the course of a "last word in list" calibration procedure, for the first 1500 msec after presentation of the beginning of the last word, wherein the light trace is the response to the last word in a congruent list, the dark trace is the response to the same last word in an incongruent list and the direction of negativity being upward from the base line.
Figure 7:
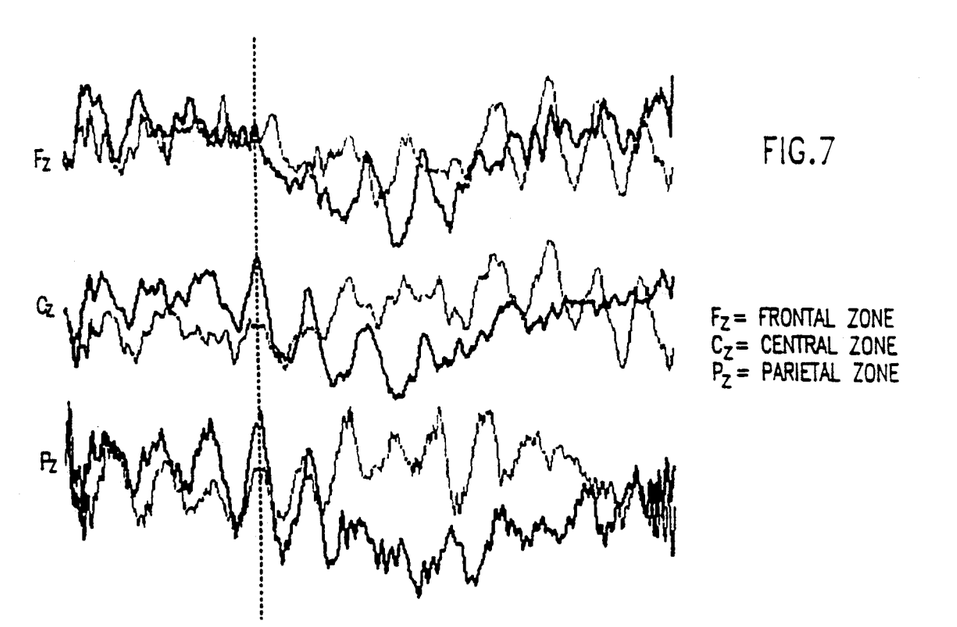
FIG. 7 shows a subject's typical EEG response, corrected for eye movement, in the course of a "last word in sentence" calibration procedure, for the first 1500 msec after the beginning of the presentation of the last word, with the light trace being the response to the last word in a congruent sentence, the dark trace being the response to the same last word in a incongruent sentence and the direction of negativity being upward from the base line.

The first calibration stage followed the Odd Ball procedure described above. The subject heard two words: Red and Green. In the first part of the Odd Ball procedure, eighty Red's and twenty Green's were presented to the subject and the subject was instructed to count the Green's. In the second part, the roles of Red and Green were reversed. As shown in FIG. 5, the EEG response to the "rare" word in each of the two parts, after correction for eye movements, displayed the typical P300 response (dark trace), while the "common" word in each part produced no ERP (light trace). In other words, the results of the first calibration stage indicated that the apparatus was functioning correctly and that the subject was producing a detectable ERP.

The second calibration stage followed the "last word in list" procedure. The subject was presented with 19 sets of four words, each repeated five times to provide a sequence of 95 sets of words. Of the 19 sets, 7 were congruent sets, 7 were incongruent sets, and 5 were control sets formed of 4 unrelated words. The sets were presented as auditory stimuli to the subject at a clearly suprathreshold intensity. A typical N400 response to an incongruent stimulus (dark trace) and congruent stimulus (light trace) is presented in FIG. 6 where the EEG has been corrected for eye movements and negativity is above the base line. The N400 response is present only for the incongruent stimulus, indicating that the subject could produce N400 to incongruent words.

The third and final calibration stage followed the "last word in sentence" procedure. The subject was presented with 88 auditory stimuli, each of which was a sentence in Hebrew, at a clearly suprathreshold intensity. In half of the sentences the final words were congruent whereas, in the remaining half of the sentences, the same final words were incongruent. In addition, 32 control sentences were presented, some of which had an incongruent final word, but the final word was not present in both congruent and incongruent sentences. The EEG responses associated with each of the final words of the sentence (both congruent and incongruent) were corrected for eye movements before the responses to congruent and incongruent stimuli were compared. Typical responses to the same last word in a congruent sentence (light trace) and in an incongruent sentence (dark trace) are presented in FIG. 7 in which negativity is above the baseline.

Following calibration, the test procedure was initiated. Five Hebrew sentences, each having two variants, were presented as auditory stimuli, where each variant was repeated ten times to the right ear of the subject. The variants were sentences which differed only in the final word such that one variant was congruent and the other variant was incongruent. The order of presentation of the sentences was randomly varied. Initially the last word of each sentence was presented at a clearly subthreshold intensity. The intensity of the last word was increased with each subsequent presentation until it was clearly suprathreshold. The corrected EEG response to each intensity was recorded.

Figure 8:
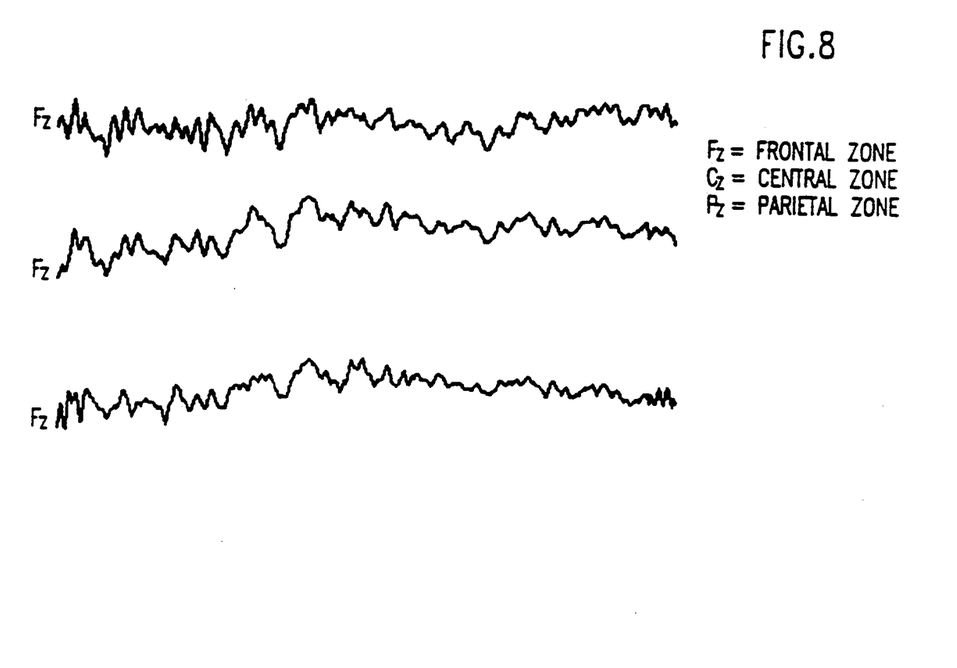
FIG. 8 shows a subject's typical EEG response, corrected for eye movement, to an incongruent last word in a test sentence presented at subthreshold intensities, for the first 1500 milliseconds after presentation of the beginning of the last word, with the direction of negativity upward from the base line.
Figure 9:
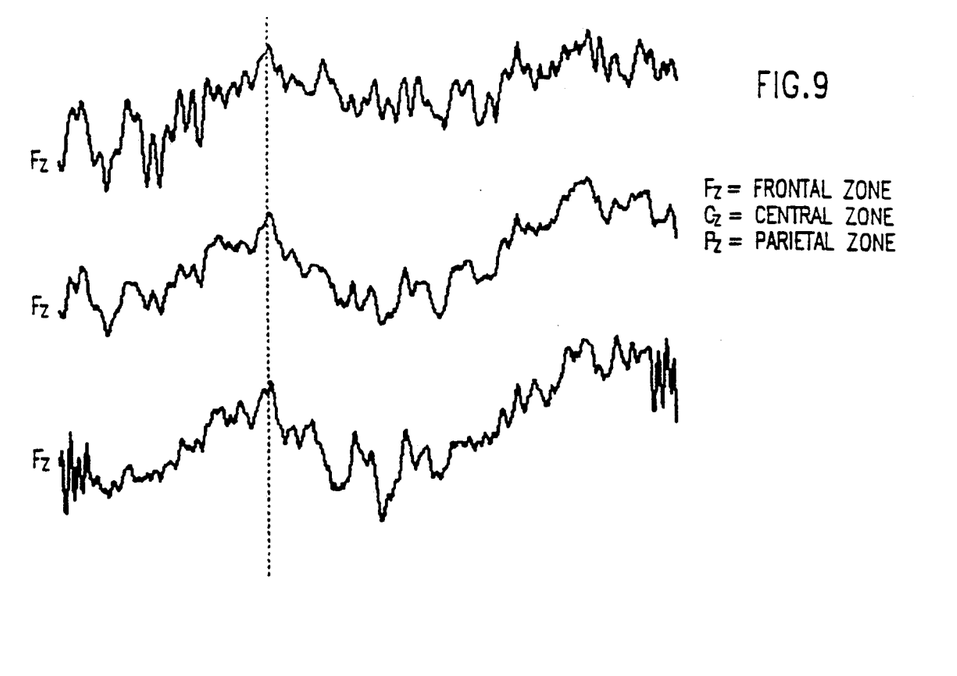
FIG. 9 shows a subject's typical EEG response, corrected for eye movement, to an incongruent last word in a test sentence presented at suprathreshold intensities, for the first 1500 milliseconds after presentation of the beginning of the last word, with the direction of negativity upward from the base line.

A typical EEG response to an incongruent last word at a subthreshold intensity can be seen in FIG. 8. It can be seen from FIG. 8 that there is no ERP at this intensity. FIG. 9 shows the EEG response to an incongruent word at a suprathreshold intensity, which can be seen to include an N400 response with the negative trace extending upward from the baseline. The auditory threshold, therefore, is the minimum stimulus intensity capable of producing the N400 response.

It will be appreciated by persons skilled in the art that the present invention is not limited to what has particularly been shown and described hereinabove. It is therefore intended that the scope of the invention be defined only by the claims which follow:

We claim:

1. Apparatus for objective determination of auditory thresholds for intelligible speech in a human subject comprising:
    means for presenting a sequence of at least one intelligible speech stimuli to a human subject at a respective sequence of stimulus intensities; and
    means for monitoring at least one physiological response of the human subject that varies with the human subject's understanding of each stimulus.

2. Apparatus according to claim 1 wherein the means for presenting comprises:
    a microprocessor for storage and recall of at least one digital stimulus signal; and
    a digital to analog converter to convert the at least one digital stimulus signal to at least one analog stimulus signal.

3. Apparatus according to claim 2 wherein the means for presenting additionally comprises means for random selection of one of a plurality of digital stimuli.

4. Apparatus according to claim 2 wherein the means for presenting comprises:
   a stimulus signal amplifier for selectively amplifying the at least one analog stimulus signal to a predetermined stimulus signal intensity.

5. Apparatus according to claim 1 wherein the means for monitoring comprises a plurality of scalp electrodes operative to monitor electrical brain activity.

6. Apparatus according to claim 1 and also comprising means for display of the monitored physiological response to a human operator, so as to enable the human operator to detect known physiological response profiles.

7. Apparatus according to claim 6 wherein the means for display includes a CRT display.

8. Apparatus according to claim 1 wherein the means for monitoring additionally comprises:
   means for correcting the monitored physiological response by substantially removing measurement artifacts.

9. Apparatus according to claim 8 wherein the means for correcting comprises:
   a suborbital electrode operative to detect electrical activity correlated with eye movements and eye blinks.

10. Apparatus according to claim 1 wherein the at least one physiological response to a presented stimulus takes a known EEG waveform when the subject understands the stimulus.

11. Apparatus according to claim 10 wherein the known EEG waveform comprises the N400 wave form.

12. Apparatus according to claim 1 wherein said means for presenting comprises a memory in which are stored at least one speech stimulus whose significance is substantially the same for any human subject who understands the speech stimulus.

13. A method for objective determination of auditory thresholds for intelligible speech in a human subject comprising the steps of:
   presenting a sequence of at least one intelligible speech stimuli to a human subject at a respective sequence of stimulus intensities; and
   monitoring at least one physiological response of the human subject that varies with the human subject's understanding of each stimulus.

14. A method according to claim 13 wherein the step of presenting comprises the steps of:
   storing and recalling at least one digital stimulus signal; and
   converting the at least one digital stimulus signal to at least one analog stimulus signal.

15. A method according to claim 14 wherein the step of presenting additionally comprises the step of random selection of one of a plurality of digital stimuli.

16. A method according to claim 14 wherein the step of presenting comprises the step of:
   selectively amplifying the at least one analog stimulus signal to a predetermined stimulus signal intensity.

17. A method according to claim 13 wherein the step of monitoring comprises the step of providing a plurality of scalp electrodes operative to monitor electrical brain activity.

18. A method according to claim 13 and also comprising the step of displaying the monitored physiological response to a human operator, so as to enable the human operator to detect known physiological response profiles.

19. A method according to claim 18 wherein the step of displaying includes the step of providing a CRT display.

20. A method according to claim 13 wherein the step of monitoring additionally comprises the step of correcting the monitored physiological response by substantially removing measurement artifacts.

21. A method according to claim 20 wherein the step of correcting comprises the step of:
   providing a suborbital electrode operative to detect electrical activity correlated with eye movements and eye blinks.

22. A method according to claim 13 wherein the at least one physiological response to a presented stimulus takes a known EEG waveform when the subject understands the stimulus.

23. A method according to claim 22 wherein the known waveform comprises the N400 wave form.

24. A method according to claim 13 wherein said step of presenting comprises the step of providing at least one speech stimulus whose significance is substantially the same for any human subject who understands the speech stimulus.

* * * * *